United States Patent
Polsky et al.

(10) Patent No.: US 6,659,937 B2
(45) Date of Patent: Dec. 9, 2003

(54) CONTINENT BLADDER ACCESS DEVICE

(76) Inventors: M. Sheldon Polsky, 13295 Hunters View, San Antonio, TX (US) 78230; Charles A. Mencio, 501 El Portal Dr., San Antonio, TX (US) 78232

(*) Notice: Subject to any disclaimer, the term of this patent is extended or adjusted under 35 U.S.C. 154(b) by 268 days.

(21) Appl. No.: 09/975,574

(22) Filed: Oct. 11, 2001

(65) Prior Publication Data

US 2003/0073880 A1 Apr. 17, 2003

(51) Int. Cl.[7] ................................................ A61F 2/02
(52) U.S. Cl. ........................................ 600/32; 623/23.68
(58) Field of Search ................... 600/29–32; 604/332, 604/335, 337; 623/14.13, 23.64, 23.65, 23.66, 23.67, 23.68

(56) References Cited

U.S. PATENT DOCUMENTS

| | | |
|---|---|---|
| 2,533,924 A | 5/1950 | Folev |
| 3,744,063 A | 7/1973 | McWhorter et al. |
| 3,815,576 A | 6/1974 | Balaban |
| 3,822,704 A * | 7/1974 | Nolan ........................ 604/339 |
| 3,854,469 A | 12/1974 | Giori et al. |
| 3,863,622 A | 2/1975 | Buuck |
| 4,167,952 A | 9/1979 | Reinicke |
| 4,222,377 A | 9/1980 | Burton |
| 4,256,093 A | 3/1981 | Helms et al. |
| RE31,121 E | 1/1983 | Reinicke |
| 4,386,601 A | 6/1983 | Trick |
| 4,417,567 A | 11/1983 | Trick |
| 4,419,985 A | 12/1983 | Trick |
| 4,428,365 A | 1/1984 | Hakkv |
| 4,552,128 A | 11/1985 | Haber |
| 4,555,242 A * | 11/1985 | Saudagar ................ 604/103.08 |
| 4,571,749 A | 2/1986 | Fischell |
| 4,587,954 A | 5/1986 | Haber |
| 4,643,169 A | 2/1987 | Koss et al. |
| 4,705,518 A * | 11/1987 | Baker et al. ................... 600/31 |
| 4,721,509 A | 1/1988 | Craggs |
| 4,784,660 A | 11/1988 | Fischell |
| 4,969,474 A | 11/1990 | Schwarz |
| 4,994,020 A | 2/1991 | Polyak |
| 5,012,822 A | 5/1991 | Schwarz |
| 5,041,136 A * | 8/1991 | Wascher et al. ............... 600/30 |
| 5,097,848 A | 3/1992 | Schwarz |
| 5,360,417 A * | 11/1994 | Gravener et al. ........... 604/278 |
| 5,520,606 A | 5/1996 | Schoolman et al. |
| 5,893,826 A | 4/1999 | Salama |
| 6,432,038 B1 * | 8/2002 | Bakane ........................ 600/29 |

* cited by examiner

*Primary Examiner*—Eric F. Winakur
(74) *Attorney, Agent, or Firm*—Gunn, Lee & Hanor, P.C.; Michelle Evans

(57) ABSTRACT

A bladder access device is disclosed that incorporates a load port and a valve connected to each other by way of a series of tubes. The valve is a four piece elliptical ring closed by a locking mechanism. The inner major axis portion of the elliptical ring has two inflatable cuffs. When fluid is injected into a self sealing and leakproof load port, the fluid flows through the series of tubes into the inflatable cuffs of the valve thus expanding them. This allows the elliptical ring to be placed around a patient's bladder and upon inflation of the inflatable cuffs, the valve closes onto the bladder allowing for continence. During this state of inflation, access can be made to the bladder by compressing the valve with two fingers. The valve closes automatically when released. The present device can be used as a closure control valve for other internal organs as well.

8 Claims, 2 Drawing Sheets

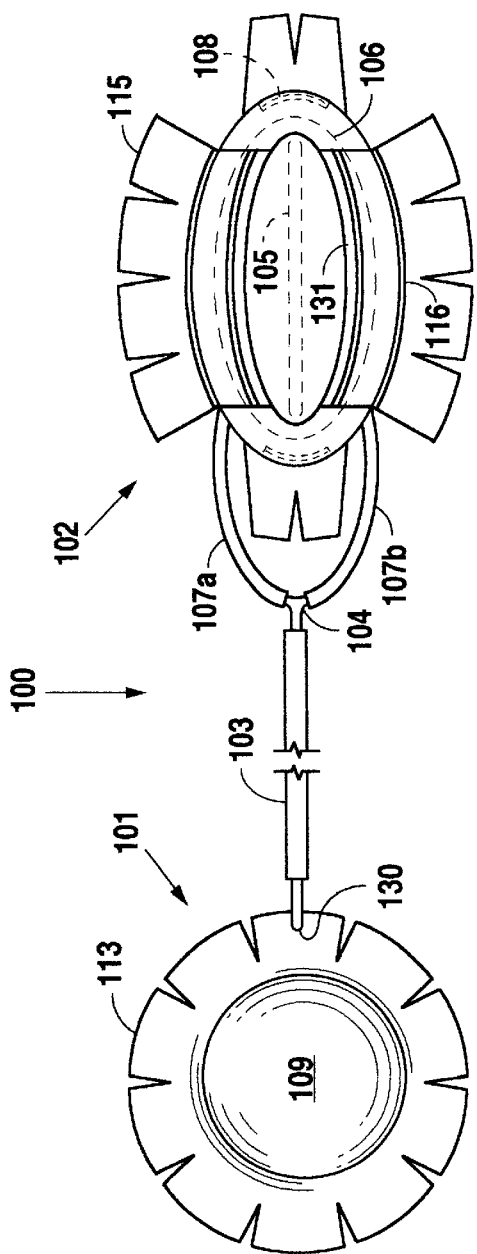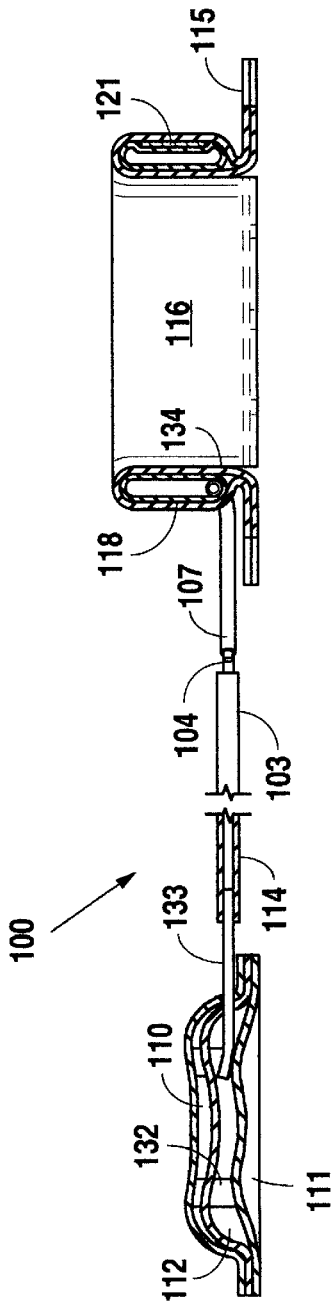

CONTINENT BLADDER ACCESS DEVICE

BACKGROUND OF THE INVENTION

1. Field of the Invention

Applicant's invention relates to a continent bladder access device. More particularly, the present invention provides for an extravesical bladder access device that can be mechanically opened to allow for urine evacuation and that self closes. There is also incorporated into the device an inflation-deflation mechanism that allows the tissue to heal and establish its blood supply prior to activation. This is accomplished through a leakproof distal port.

2. Background Information

Urinary incontinence is a major health issue that affects an estimated 10 million patients to some degree. Fifteen to thirty percent of women over age 65 in retirement communities suffer from urinary incontinence. These problems can be treated with both medications and surgery.

However, a more difficult problem in the general population, and in particular the geriatric population, is urinary retention. Since these patients will at times have overflow incontinence, they are often thought of as incontinent patients, whereas in reality they are unable to empty their bladders. In the nursing home population, patients are often chronically catheterized, since intermittent catheterization by hospital personnel is time consuming. Often these patients are unable to fully cooperate to allow such intermittent catheterization.

Catheter-related urosepsis is the most common source of gram-negative bacteremia in patients requiring hospitalization. Furthermore, urosepsis accounts for between 8 to 30% of all nursing home transfers to acute facilities.[1] One can only imagine the annual cost to private insurance companies, Medicare and Medicaid.

Chronic urinary retention in the male patient can be due to prostatic obstruction. However, a significant number of elderly male patients, often in nursing facilities, are still unable to void even after prostatic surgery. Both male and female patients often have urinary retention secondary to neural injury to the sacral portion of the cord or to the motor or sensory roots of the corda equina. This can be due to trauma, tumors, discogenic disease, tabes dorsalis, or congenital abnormalities such as meningomyelocele. Certain metabolic diseases, such as diabetes and pernicious anemia, can also affect the peripheral nerves and lead to a flaccid neurogenic bladder. These bladder problems are often aggravated, especially in men by prostatic obstruction. Associated pelvic floor muscle relaxation often causes overflow incontinence as well. Certain medications which may be essential for patient management, such as psychotropic and antihistaminic drugs, exert an anticholinergic effect on the bladder and may also add insult to injury.

At times, conditions such as multiple sclerosis may cause a dyssynergia of the bladder and external urethral sphincter, which is unable to relax sufficiently to allow the bladder to empty. This too can be a cause of urinary retention.

Thus, the two options of treating these patients with chronic urinary retention are intermittent catheterization, which can be done at home by the patient or family members, or some form of chronic catheterization either via the urethra or with a suprapubic catheter. With either of these methods, a foreign body is introduced chronically into the bladder, which if left in place without periodic changing will cause calcific encrustations to form on the internalized portion of the catheter. Also, everyone with an indwelling catheter will eventually have their bladder urine colonized with bacteria, which not infrequently, especially in immobile patients, may lead to urosepsis—a potentially life threatening condition.

The present invention alleviates these problems of the prior art by providing for a continent bladder access device. The present invention allows easy access to the bladder for emptying, yet at the same time achieves continence for the benefit of the patient, the family, and nursing staff. It incorporates a self-sealing load port and a valve connected to each other by way of a series of tubes. The valve is an extravesical four piece elliptical ring composed of two distinct pairs of opposing sections. A pair of rigid locking mechanisms closes the ring at the ends of the major axis. A pair of semi-rigid sections parallel the major axis. These two longitudinal sections feature opposing matching inflatable cuffs. After surgical implantation and requisite healing, the valve may be opened by finger pressure at the ends of the major axis, closing automatically upon release. Since a portion of the full-thickness bladder is brought through the center of the valve, cut, draped over it and sutured to the skin during the surgical procedure, there must be no compromise of blood supply to this portion of the bladder. While everything is healing, no pressure should be applied to the area. At a later date when the tissue is healed and blood supply established, the permanent opening in the bladder is controlled by the inflatable cuffs. Fluid is injected into the load port and the fluid flows through the series of tubes into the inflatable cuffs of the valve, thereby closing it at safe tissue pressures to achieve continence. When fluid is removed from the load port, the fluid is removed from the inflatable cuffs contracting them back toward their resting state. This allows for relaxation of the inflatable cuffs away from the bladder when an adjustment to the valve is necessary. Should fluid need to be added or removed, it can be done as an office procedure at any time by means of the self-sealing load port. For drainage, one need only push on each end of the valve causing the cuff section to open slightly. A catheter can now be inserted to drain the bladder.

The present invention can also be used as a closure control valve for other internal tubular organs, such as bowel or urethra.

This invention and its surgical method of insertion into the patient are less drastic than the prior art. The present device is not as complicated to insert and maintain as the devices of the prior art. Since the device is less complicated, the time it takes to insert such a device in surgery is significantly decreased. In addition, the device is designed to initially exert very low pressures on the healing tissues. Once healed, the inflatable cuffs can be activated for continence. Most importantly, the valve itself—a foreign body—does not come in contact with the inside lining of the patient's bladder. There is no possibility for valve encrustation to occur, and the potential for urosepsis is greatly reduced. The device is also simple enough for family members and nursing personnel to operate. Overall this present device and its method of insertion leads to reduced stress to the patient with reduced risk of infection or follow-up surgery.

SUMMARY OF THE INVENTION

It is an object of the present invention to provide a novel continent bladder access device.

It is another object of the present invention to provide a novel continent bladder access device that incorporates a valve to control access to the bladder.

Another object of the present invention is to provide a novel continent bladder access device that incorporates a valve with an elliptical shaped ring for placement around the bladder to control access to the bladder.

Yet another object of the present invention is to provide a novel continent bladder access device that incorporates a valve with an external elliptical shaped ring and an internal inflatable cuff system.

It is another object of the present invention to provide a novel continent bladder access device that incorporates two equal and opposite inflatable cuff sections which are joined by a locking mechanism at each end. The locking mechanisms provide fulcrum points for manually relaxing cuff pressure by deflecting the external elliptical ring.

An additional object of the present invention is to provide a novel continent bladder access device that incorporates a load port for injection of fluids into the interior inflatable cuff sections of the valve. This provides a means by which the bladder access device can be activated after healing and adjusted if the patient's bladder thickness changes—without surgery.

An additional object of the present invention is to provide a novel continent bladder access device that can be surgically implanted with less stress on the patient.

Another object of the present invention is to provide a novel continent bladder access device that allows healing after surgical implantation without pressure on the bladder or surrounding tissue thus preventing tissue necrosis.

Still another object of the present invention is to provide a novel continent bladder access device that does not maintain any foreign body within the bladder which would cause urinary infection and encrustation of the foreign body.

Another object of the present invention is to provide a novel continent bladder access device that utilizes a valve that does not come into contact with the urine within the bladder, but allows access to the bladder.

In satisfaction of these and related objectives, Applicant's present invention provides for a continent bladder access device having a load port connected to a control valve by way of a series of tubes. Applicant's invention permits its practitioner to control access to a patient's bladder by way of a control valve. Upon compressing the ends of the major axis of the elliptical valve with two fingers access can be achieved. When the valve is released, the valve closes automatically.

BRIEF DESCRIPTION OF THE DRAWINGS

FIG. 1 is a top view of the preferred embodiment of the present invention.

FIG. 2 is a cross sectional side view of the preferred embodiment of the present invention.

DESCRIPTION OF THE PREFERRED EMBODIMENT

Figure 3:
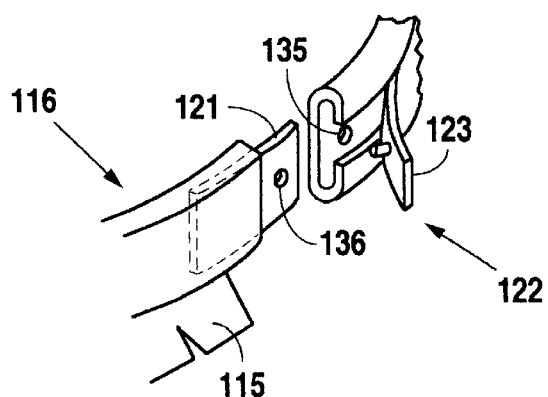
FIG. 3 is a detailed view of the locking mechanism of the preferred embodiment of the present invention.

Referring to FIG. 1, a top view of the preferred embodiment of the present bladder access device 100 is shown. A load port 101 is connected to a valve 102 by way of a tubes 103, 107a and 107b. The load port 101 can be of any size and shape suitable for its application, but is preferably round, self-sealing, and leakproof. The diameter of the load port 101 of the present invention is 6.0 cm with a thickness of 1.0 cm. Load port 101 is preferably domed, being flatter at its outer diameter edges 113 than at its center 109. The outer diameter edges 113 are preferably fringed to allow for ease of attachment to surrounding tissues within the patient; however, any design capable of accomplishing this task can be used. The outer diameter edges 113 of the present invention were designed using reinforced Silastic™ sheeting. Load port 101 is preferably made from a medical grade material and is designed to allow for injection of fluids into the center 109 for distribution to the valve 102 to regulate pressure within the valve 102 without leakage of the fluids from load port 101 into the surrounding environment.

Tube 103 is connected at one end into exit point coupler fitting 130 of load port 101. This tube 103 is preferably made of a medical grade material such as silicone. Tube 103 can be of any length and diameter suitable for the present application. The dimensions of tube 103 found to be preferred for the present invention were a diameter of 5 mm and a length of 13 cm. At the opposite end of tube 103 is a first point connection to a Y fitting 104. This Y fitting 104 and coupler fitting 130 can be made of any medical grade material with angles and diameter suitable for the present application, including, but not limited to, stainless steel.

The remaining two point connections of the Y fitting 104 connect to tube sections 107a and 107b. Tube 107a is connected to an interior cuff of one side of elliptical ring 116. Similarly, tube 107b is connected to the opposite side. Tubes 107a and 107b are preferably made of a medical grade material such as silicone. Tubes 107a and 107b can be of any length and diameter suitable for the present application. The dimensions of tubes 107a and 107b found to be preferred for the present invention are of a diameter of 5.0 mm and a length of 4.0 cm. Tubes 107a and 107b are connected at their opposite ends to valve 102. Tubes 103, 107a and 107b act to transport fluids from load port 101 to valve 102 to regulate pressure within valve 102.

Figure 5:
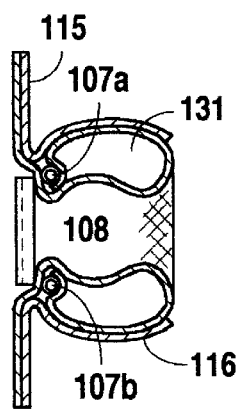
FIG. 5 is vertical minor axis cross section of the elliptical ring of the present invention showing complementary profiles of cuff inner walls.

Valve 102 can be of any size and shape suitable for the present application, but preferably exists as a four piece extravesical elliptical ring 116. In the present invention at rest, the width of the major outer axis of valve 102 was 6.5 cm, the width of the minor outer axis was 3.5 cm, the width of the major inner axis (before inflation) was 5.0 cm, and the width of the minor inner axis (before inflation) was 1.5 cm. The height and thickness at rest of elliptical ring 116 is 2.5 cm and 1.0 cm respectively. The two opposing cuff sections of elliptical ring 116 are joined at each end by a locking mechanism 108. These mechanisms are constructed of medical grade rigid structural plastic and stainless steel spring leaf. The outer perimeter longitudinal portions of elliptical ring 116 at the cuff sections is flexible to semi-rigid. In the present invention, thin-gauge stainless steel spring leaf was used, clad inside and outside with reeinforced Silastic™ sheeting. The inner sides of sections of elliptical ring 116 on the major axis have inflatable cuffs, 131. The cuffs oppose each other in a complimentary ogee curve, as shown in FIG. 5. Inflatable cuffs 131 are capable of receiving fluid that is injected into load port 101 from tubes 103, 107a and 107b. Fluid can be removed by the same route. When no fluid is within the inflatable cuffs 131, it is in a state of rest at point 106 giving maximum volume within the inner portions of elliptical ring 116. Upon introduction of fluid into cuffs 131, the inflatable cuffs 131 can expand toward each other to point 105, creating a much smaller volume within elliptical ring 116.

During the surgical procedure to implant the present invention, a portion of the full-thickness bladder is brought to the center of valve 102, cut, draped over valve 102 and sutured to the skin. Therefore, there is no compromise of blood supply to this portion of the bladder. No pressure is applied to the area while healing. After healing, the permanent opening in the bladder is controlled by inflatable cuffs 131, expanded at safe tissue pressures to achieve continence. While in this inflated state, access can be made to the patient's bladder by way of valve 102 by compressing the ends of the valve with two fingers. A catheter could be inserted at this time to drain the bladder and promptly removed after drainage. When the valve 102 is released, the valve 102 closes automatically. When fluid is removed from inflatable cuff 131, inflatable cuff 131 can be deflated down to its state of rest at point 106. The amount of inflation and deflation will obviously vary based on the needs of the individual patient.

At the base of elliptical ring 116 are outer edges 115 which are preferably fringed to allow for ease of attachment to surrounding tissue within the patient. However, any design and dimensions capable of accomplishing this task can be used. Outer edges 115 are preferably made from a medical grade material. The outer edges 115 of the present invention were designed using reinforced Silastic™ sheeting.

FIG. 2 illustrates a cross sectional side view of the preferred embodiment of the present bladder access device 100. Again, load port 101 is shown connected to valve 102 by way of tubes 103 and 107. A cross section of load port 101 shows that it is composed of multiple layers which can be of any suitable dimensions. These layers include a bottom layer 111, a middle layer 112, and a top layer 110. Other layers may be used as well. The thickness of the layers in the preferred embodiment of the present invention is 1 mm for the bottom layer 111, 5 mm for the middle layer 112, and 5 mm for the top layer 110.

Within middle layer 112 and top layer 110 are structural plastic rings 132 to provide rigidity preferably having dimensions suitable for the present application.

Bottom layer 111 consists of rigid, non-penetrable, molded material suitable for a needle barrier. The dimensions of the plastic ring 132 in middle layer 112 of the preferred embodiment of the present invention are 30 mm in diameter and 5 mm thick, while the dimensions of the plastic ring 132 in top layer 110 of the present invention are 30 mm in diameter and 5 mm thick. Plastic ring 132 in top layer 110 is filled with a flexible medical grade gel, such as but not limited to silicone.

One end of inner tubing 133 is located within plastic ring 132 of middle layer 112 of load port 101. Inner tubing 133 is preferably made from a rigid medical grade material. Inner tubing 133 can be of any length and diameter suitable for the present application. The dimensions of inner tubing 133 preferred for the present invention are 2 mm in diameter and a length of 30 mm. The opposing end of inner tubing 133 extends out of exit point 130 and is joined at its opposite end to tube 103 by way of a tube connection fitting 114. The cross sectional view of valve 102 shows one piece of the two piece elliptical ring 116 with the locking mechanism 108 removed. Elliptical ring 116 is composed of two layers, an inner layer 118 and an outer layer 134. The inner layer 118 is composed of Silastic™ plastic sheeting which is flexible. The outer layer 134 is semirigid, consisting of a composite lamination of Silastic™ sheeting and thin-gauge stainless steel spring leaf. Inner layers 118 of the inflatable cuffs 131 are designed to receive fluid from tubes 107a and 107b introduced through load port 101.

Figure 4:
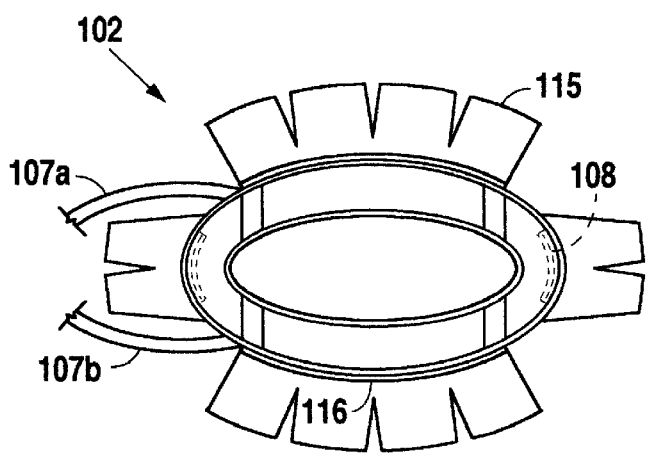
FIG. 4 is a horizontal, major axis cross section of the elliptical ring of the present invention with the locking mechanism in place.

The surgical procedure for insertion of the bladder access device 100 of the present invention into a patient involves a superpubic incision. When the bladder access device 100 is needed, the surgeon will place both pieces of elliptical ring 116 together around the patient's bladder and secure the locking mechanism 108. The locking mechanism 108 can also be secured to the elliptical ring 116 pieces before introduction to the bladder. The locking mechanism 108 is illustrated in more detail in FIG. 3. Each piece of the elliptical ring 116 has at one end a leaf spring 121 and at the opposing end a fulcrum unit link 122 with a lock 123 attached thereto. Each fulcrum unit link122 can be of any rigid medical grade plastic. Phenolic was used in the present invention. Each fulcrum unit link 122 has a T-slot recess with a dowel pin hole 135 at its inner portion. Hinged by a leaf spring from the back of fulcrum unit link 122 is lock 123 from which a steel dowel pin projects down, aligned with hole 135. The two pieces of the elliptical ring 116 are locked together by the insertion of leaf spring 121 into the T-slot recess of the fulcrum unit link 122 with a central hole 136 of leaf spring 121 being located over the corresponding hole 135 at the inner portion of fulcrum unit link 122. To lock the ring 116 pieces together, the projecting dowel pin of lock 123 is closed down into dowel pin hole 135 through the leaf spring 121 and locked by its hinge spring. A cross section of the elliptical ring 116 with the locking mechanism 108 in place is shown in FIG. 4.

Once the valve 102 of the bladder access device 100 is in place around the bladder of the patient, it is secured to the surrounding tissue within the patient by way of the outer edges 115. The load port 101 is then placed at a remote location, such as the superior iliac spine, within the patient's body that will allow access by health care practitioners or the patient to inject fluid into the center 109 to inflate the inflatable cuff 131 without surgery at a later date when the surgical site has healed. The load port 101 is then secured to the surrounding tissue within the patient by way of the outer diameter edges 113.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A continent bladder access device comprising:
    a first piece of a valve having a first end and a second end;
    a second piece of said valve, having a first end and a second end, connected to said first piece by way of a locking mechanism to form a two piece valve, said two piece valve having inflatable cuffs located within its inner portions;
    a load port connected to said two piece valve by way of at least one tube;
    whereby when said first piece and said second piece of said valve are placed around said bladder and locked to complete said valve, access can be controlled to said bladder.

2. The continent bladder access device of claim 1 wherein said at least one tube connects to said inflatable cuffs such that when fluid is introduced into said load port, said fluid travels through at least one tube into said inflatable cuffs causing inflation allowing for continence of said bladder.

3. The continent bladder access device of claim 2 wherein said load port comprises at least one layer to render said load port self sealing and leakproof.

4. The continent bladder access device of claim 3 wherein said locking mechanism comprises:
- a fulcrum unit lock on said first end of said first piece of said valve and said second end of said second piece of said valve; and
- a leaf spring on said second end of said first piece of said valve and said first end of said second piece of said valve;
- whereby said leaf spring on said second end of said first piece of said valve is in contact with said fulcrum unit lock of said second end of said second piece of said valve and said leaf spring of said first end of said second piece of said valve is in contact with said fulcrum unit lock of said first end of said first piece of said valve.

5. The continent bladder access device of claim 4 wherein said load port comprisings rings to provide rigidity in the layers of said port.

6. The continent bladder access device of claim 5 further comprising attachment edges along the outer diameter of said load port for attachment of said load port to surrounding tissues within the patient.

7. The continent bladder access device of claim 6 wherein said at least one tube is connected at one end into an exit point of said load port.

8. The continent bladder access device of claim 7 wherein at least one tube branches at its opposite end to a Y.

* * * * *